(12) United States Patent
Thompson

(10) Patent No.: US 7,614,401 B2
(45) Date of Patent: Nov. 10, 2009

(54) NASAL CANNULA ASSEMBLY

(75) Inventor: Paul S. Thompson, 11472 Tree Hollow La., San Diego, CA (US) 92128

(73) Assignee: Paul S. Thompson, San Diego, CA (US)

( * ) Notice: Subject to any disclaimer, the term of this patent is extended or adjusted under 35 U.S.C. 154(b) by 872 days.

(21) Appl. No.: 10/634,369

(22) Filed: Aug. 6, 2003

(65) Prior Publication Data

US 2005/0033247 A1 Feb. 10, 2005

(51) Int. Cl.
*A61M 16/00* (2006.01)

(52) U.S. Cl. .............................. 128/207.18; 128/204.12

(58) Field of Classification Search ............ 128/207.18, 128/207.13, 206.18, 200.24, 200.26, 203.22, 128/204.12, 206.28, 206.11, 911, 912, DIG. 26
See application file for complete search history.

(56) References Cited

U.S. PATENT DOCUMENTS

| 2,693,800 | A |   | 11/1954 | Caldwell |
|---|---|---|---|---|
| 2,735,432 | A |   | 2/1956 | Hudson |
| 2,763,263 | A | * | 9/1956 | Ellman ................. 128/203.13 |
| 2,868,199 | A |   | 1/1959 | Hudson |
| 2,931,358 | A |   | 4/1960 | Sheridan |
| 3,400,714 | A |   | 9/1968 | Sheridan |
| 3,513,844 | A |   | 5/1970 | Smith |
| 3,643,660 | A |   | 2/1972 | Hudson et al. |
| 3,802,431 | A |   | 4/1974 | Farr |
| 4,106,505 | A |   | 8/1978 | Salter et al. |
| 4,422,456 | A |   | 12/1983 | Tiep |
| 4,753,233 | A |   | 6/1988 | Grimes |
| 4,915,104 | A |   | 4/1990 | Marcy |
| 5,222,486 | A |   | 6/1993 | Vaughn |
| 5,438,979 | A |   | 8/1995 | Johnson, Jr. et al. |
| 5,533,506 | A |   | 7/1996 | Wood |
| 5,704,916 | A |   | 1/1998 | Byrd |
| 5,797,627 | A |   | 8/1998 | Salter et al. |
| 6,328,038 | B1 |   | 12/2001 | Kessler et al. |
| 2002/0092527 | A1 | * | 7/2002 | Wood .................... 128/207.18 |

* cited by examiner

*Primary Examiner*—Steven O Douglas
(74) *Attorney, Agent, or Firm*—Mark Wisnosky

(57) ABSTRACT

A nasal cannula that combines extremely flexible tubing and a novel vee-shaped nosepiece that fits the contour of the face and provides a stable footing and is self-righting because more than half its weight is below the tubing attachment points. Gas delivery prongs are molded at an angle relative to the body to direct gas into the center of the nostrils. The tubing is made from ultra-high molecular weight PVC resin with hardness between 40 and 75 Shore A.

24 Claims, 11 Drawing Sheets

A

B

C

D

NASAL CANNULA ASSEMBLY

BACKGROUND OF INVENTION

Oftentimes a patient will require a continuous oxygen supply while at a medical facility or while at home under medical care. Oxygen delivery devices, such as the cannula, are well known in the medical arts. The typical means and method for attaching an oxygen supply cannula to a patient's nostrils involves attaching a pair of oxygen supply lines to the cannula and inserting the appropriate portions of the cannula into the patient's nostrils. Next, the oxygen supply lines are wrapped around the patient's ears and the remaining portions of the oxygen supply lines are left to hang below the patient's chin, where an adapter couples the two oxygen supply lines into a single oxygen supply line. Additionally, below the chin of the patient, most systems use a slide connector to hold the two supply lines snugly against the patient's neck.

The problems with the prior art arrangement are many and significant. First, the reason that the oxygen supply lines are wrapped around the patient's ears is to provide a support for the oxygen supply lines, as well as for the cannula attached thereto. Thus, in order to have the cannula smartly fitted into the patient's nostrils, as desired, the oxygen supply lines are typically wrapped quite tightly about the patient's ears and this is very painful for the patient. In response, some patients use a cushion around portions of their ears in order to mitigate the pain associated with having the oxygen supply lines so tightly tethered to their ears. Additionally, the tubing across the face leaves an unsightly, deep and irritating impression that becomes semi-permanent so long as the oxygen therapy continues. These impressions in the face of the patient are cosmetically undesirable and, in some cases, the pressure exerted by the tubes against the upper cheeks tends to force the patient's eyes closed, thus interfering with clear vision and causing watering of the eyes.

Another serious problem associated with the typical cannula oxygen supply system described above and with other previous designs is that the weight of the cannula results in a tendency to fall out of the patient's nostrils. For some patients this is simply unacceptable. Thus, they wrap the oxygen supply lines around their ears extremely tightly and they snug the lower portions of the oxygen supply lines very firmly against the neck. Accordingly, continued contact of the cannula, especially at the philtrum and around the unprotected upper lip and cheek areas causes inflammation and irritation and ulcerous conditions may occur after a period of time. Not only does the wearer inadvertently move the cannula while sleeping as the head moves from side to side, but also when eating and/or talking, further movement occurs.

The central section of prior art cannulas is a straight horizontal form that contacts the wearer at a small point in the center of the nasalabidial area (FIG. 6A). The cannula can easily tilt to the side allowing the hollow tubular nasal extensions, or nares, to come out of the nostril, contact the nasal walls or direct gas against the wall, all of which are a common source of discomfort. The nares of prior art cannulas are curved when viewed from then side but are essentially parallel to each other looking from the front, as shown in FIG. 6A. The triangular shape of the nose causes the outer walls of the nostrils to slope inwards and the tips of the nares can contact the walls even if the cannula does not tip to the side. Gas is often directed against the nasal walls and dries the mucous tissues causing ulcerous sores. It is important for comfort that the cannula be positioned on the face in such a way that the nares are located in the nostril away from the walls and gas is directed into the open area of the pharynx.

The tips of the nares deflect hairs inside the nostrils causing an unpleasant sensation that is especially disconcerting to a patient not accustomed to wearing these devices. Oftentimes the patient removes the cannula thus eliminating the benefit of supplemental oxygen.

The tendency for cannulas to move, tilt or roll comes from a number of forces acting on the cannula. Gravity acts to make the cannula fall out but it can also cause it to roll out of the nostrils on cannulas with a high center of gravity. Most, if not all prior art cannulas have a high center of gravity due to the weight of the nares and half the body located above the support tubing attachment point.

The majority of the force acting to urge the cannula out of position comes from the very tubing whose job it is to support the cannula. Insufficient flexibility and "memory" of the PVC tubing cause forces acting on one end of the tubing to affect the cannula at the other end. Insufficient flexibility, or stiffness, increases the force needed to bend the tubing when the head or parts of the face are moved and the cannula reacts to these forces by lifting off the face or tilting to the side.

Memory is a term describing the tendency for the tubing to "take a set" or adopt a shape after a period of time. This can easily be seen when a coiled cannula is first removed from its package and resembles a spring. FIG. 10 illustrates the shape adopted by tubing 29 when the cannula is worn on the head and acts like a frame attempting to hold the cannula in a fixed position. However, when the head is turned the nose drags the cannula along. The various rubbing actions that occur with each movement cause red spots and irritation under the nose and on the ears.

The support tubing is made from PVC, or polyvinyl chloride with a hardness of about 80 to 85 durometer Shore A that gives it a relatively high stiffness in torsion that makes it difficult to twist at one end if the other end is held rigid. Prior art cannulas make use of this stiffness to prevent the top-heavy cannulas from rolling over. The far ends of both support tubes are held rigid by bonding them side-by-side to a common coupling then the cannula is rotated to a predetermined angle and the remaining ends of the support tubes are bonded to each side. If the predetermined angle is correctly set then the nares will properly direct gas flow into the nasal cavity and the stiffness of the tubing will prevent rotation of the cannula. Unfortunately the correct angle for comfort is a fairly narrow range and the predetermined angle is set by hand so a significant number of cannulas do not fit well. An integral tab in the cannula body is designed to rest against the lip to rotate the cannula back into position by twisting the tubing and this can be a source of irritation.

FIG. 8 is a depiction of a step in the manufacturing process of prior art cannulas where the nares of the cannula are set at angle F before the tubes 29 are bonded 28 to fork connector 5. FIG. 9 shows how the tubing supports the cannula with the nares pointed in the correct direction when worn on the face of an individual. FIG. 10 illustrates how forcing the nares to a different angle causes the tubing to twist. Upon removal of the force, the nares snap back to their original position.

FIG. 6A shows a common injection molded prior art cannula with an integral tab intended to bear against the lip to limit rotation if the tubing does not point the nares properly. The main body is a horizontal hollow tube with support tubing bonded to each open end. The important point to note is that the support tubes are bonded directly in line with the rotational axis of the cannula body. All cannulas of this style rely on tubing stiffness to control the pointing angle of the nares.

The reasons generally given for using tubing of a specific hardness is that it is needed to resist crushing as might happen when a person is sleeping with the tubing pressed between their face and a pillow and secondly, the tubing must be sufficiently hard to resist kinking when the head is moved about. In general, the role tubing stiffness plays in preventing rotation is not well known in the field and does not appear in literature or in patents.

The invention described in U.S. Pat. No. 4,106,505 (Salter) uses a different method to orient the nares. It has a main body that is tall and narrow so that tension from the tubing bends the thin section of the cannula body around the upper lip to form a U-shape when viewed from above. The nares project from the body in the tall or vertical direction then curve toward the nasal passages so they are always pointed properly. Although undesirable tension is required to bend the cannula body, this style of prior art cannula does not require torsional rigidity to orient the nares and, in fact, the torsional rigidity can actually interfere with proper pointing in cases where the tubing is bonded such that it tries to rotate the cannula at some other angle.

The main supply tubing is generally made from the same material as the support tubing and also causes a number of problems in prior art cannulas. Regular PVC used in prior art cannulas have poor low temperature flexibility and become very stiff outside in the winter and have even been known to snap in two. It also has poor compression set properties that give it memory. The coil shape that remains after the cannula is removed from the package looks and acts like a spring that tries to pull back when extended. The constant force prevents the tubing from laying or draping nicely. Due to the stiffness of the material, movements that should only affect a small section of tubing, instead, involve longer sections that increase the likelihood of catching or entangling on some object.

This same characteristic also causes the main supply tubing to form twisted loops that kink and block the flow of oxygen, particularly in longer lengths. In the home, oxygen users usually have a central source of oxygen and use a long hose to supply oxygen at some distance from the source. This can be an integral part of the cannula in lengths up to 35 feet but, in many cases, the long length of main supply tubing is detachable so it can be reused when the cannula is changed. A coupler is used to connect the two pieces together as shown in FIG. 11.

The coiled shape acquired in the package never goes away completely and when the tubing is stretched out across the floor there will be small periodic humps rising slightly above the floor. These humps increase the chance of the tubing becoming caught under foot or entangled and they are also the reason that it is so common for prior art tubing to form twisted loops that eventually cut off the oxygen supply. The humps raise the tubing off the floor enough to provide the leverage to roll the tubing when it is dragged sideways across carpeting and wind it up. At some point the tubing relieves the stored energy by spinning a section of tubing into a spiral twisted loop like the twisted pile of a carpet. Eventually the tubing becomes kinked at the apex of the loop where the tubing makes a u-turn and heads back. This blocks the flow of oxygen and even when the twists are removed, the site of the kink is a weak spot that tends to encourage future kinking. Various swivel connectors have been developed to prevent this problem but they cause problems themselves by becoming caught in doorjambs or on furniture legs as they are dragged along.

A number of patents have been issued that were intended to solve one or more of the problems just discussed. One of these, U.S. Pat. No. 5,509,409, describes a plate-like face guard intended to protect the face from developing grooves caused by the tubing. U.S. Pat. Nos. 4,699,139, 4,949,733 and 6,026,811 are inventions for tubing pads to protect the ears while U.S. Pat. No. 5,025,805 is a tubing pad that protects both the face and the ears. U.S. Pat. Nos. 5,636,630 and 4,753,233 route the tubing to avoid the ear. U.S. Pat. Nos. 6,328,038, 6,505,624, 4,808,160, 4,836,200, 4,915,104, 4,995,384, 4,422,456, 5,704,916, 4,156,426, 4,660,555, 4,406,283, 5,438,979, 4,739,757, 5,188,101 and 4,367,735 all describe various straps or supports to hold the cannula in position. U.S. Pat. Nos. 5,113,857 and 5,794,619 are for devices that clip to the columella to secure the cannula. U.S. Pat. No. 5,526,806 is for a cannula without nares to avoid irritation inside the nostrils. U.S. Pat. Nos. 4,875,718, 5,222,486, 5,284,134, 5,572,994 and 5,797,627 are for swivel connectors to prevent twisting of supply tubing.

Therefore, there exists a need to provide a means for reliably attaching an oxygen cannula to a patient's nostrils without forming grooves in the cheeks or irritating the ears, the nasalabidial area, inside the nostrils and under the neck. Further, there is a need for a cannula to fit properly when first removed from the package and reduce the storage space needed to maintain a cannula inventory. There is also a need for cannulas that can be comfortably used in cold temperatures and main supply tubing that does not form twisted loops.

SUMMARY OF INVENTION

A nasal cannula assembly with a nasal cannula that is lightweight, small in size, stable in position with nares that positively guide the gas flow along the natural contours of the nasal passages and are barely felt by the wearer. Extremely flexible support tubing that reliably orients and positions the cannula with little or no tension on the face and flexible main supply tubing that is very manageable, remains flexible at low temperature and has little tendency to form twisted loops that block flow.

The nasal cannula assembly just described is a combination of three inventions, (i) cannula (ii) support tubing (iii) main supply tubing, that provide a new product that markedly improves comfort to the wearer. Each invention can be used independently or in various combinations to improve comfort and utility of prior art nasal cannula assemblies.

The first invention is a vee-shaped cannula, or nosepiece that conforms to the natural contours of the face and improves the fit and comfort and has nares with extremely flexible tips that curve inward to prevent either the tips or the gas flow from hitting the walls. The flexible rim at the tips will yield to nose hairs instead of disturbing them thus eliminating sensation. This cannula offers a significant improvement in comfort when used with prior art support tubing.

The second invention is support tubing with specific properties that work in concert with the shape of the cannula to reduce tubing tension to a bare minimum yet secure the placement of the cannula. It is made from an ultra-high molecular weight PVC resin that gives it rubber-like qualities such as resilience, extreme flexibility and low compression set yet bonds with solvent like regular PVC and remains flexible at low temperatures. This support tubing can be used with all cannulas that do not rely on torsional stiffness from the support tubing to maintain the rotational orientation of the cannula body. The low force required to coil the tubing for packaging allows the cannula to be thinner and lighter without kinking in the package.

The third invention is main supply tubing made from the same or similar material as the support tubing. The flexibility and resilience allow it to lay flat like wet spaghetti so that it is very manageable and is highly resistant to forming the twisted loops common with prior art tubing. The material has very good low temperature flexibility and improves the utility of the cannula when outside in a cold environment. This material can be used for the main supply tubing of any type of cannula or support tubing.

The basic structure of the assembly and its use is described at the beginning of the background section. For purposes of this patent, the most common single style of cannula and method of use will be described but should not be considered a limitation. The inventions described here have been applied to a broad range of uses such as: (a) miniaturized cannulas with smaller tubing (b) cannulas for premature and full term infants (c) cannulas for use with breath demand systems (d) cannulas for sleep apnea studies (e)cannulas for exhaled gas studies (f) cannulas with a variety of body diameters (g) cannulas with a variety of nare diameters and spacing (h) cannulas for people with deviated septums and (i) cannulas with integral swivels.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways.

Also, it is to be understood that the phraseology and terminology employed herein are for the purpose of descriptions and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF DRAWINGS

FIG. 6A shows the proximity of the uncurved nares to the nasal walls and the clearance that can let the cannula tip sideways. FIG. 6B is the improved cannula that closely matches the natural contours of the nose to prevent rocking and has inwardly curved nares to provide additional clearance from the nasal walls as well as directing gas into the nasal cavity.

DETAILED DESCRIPTION

Figure 1:
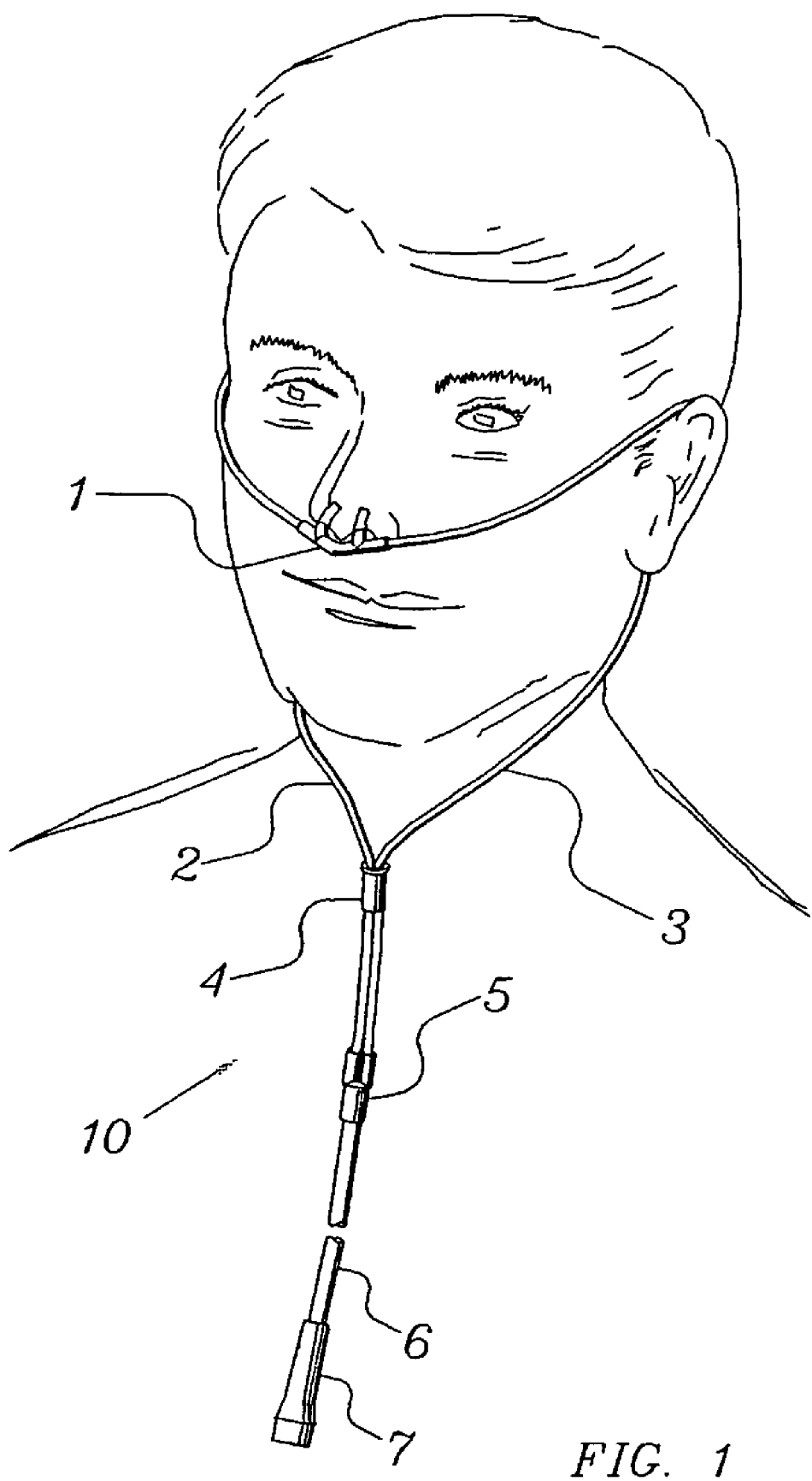
FIG. 1 is a front perspective view of the cannula of the present invention as worn by a patient. Item 1 is the cannula, Items 2 and 3 are support tubes, Item 4 is a slide used to tighten the tubing against the neck, Item 5 is a fork connector to divide gas flow between support tubes 2 and 3, Item 6 is the main supply tubing and Item 7 is a connector that couples to the oxygen source.
Figure 3:
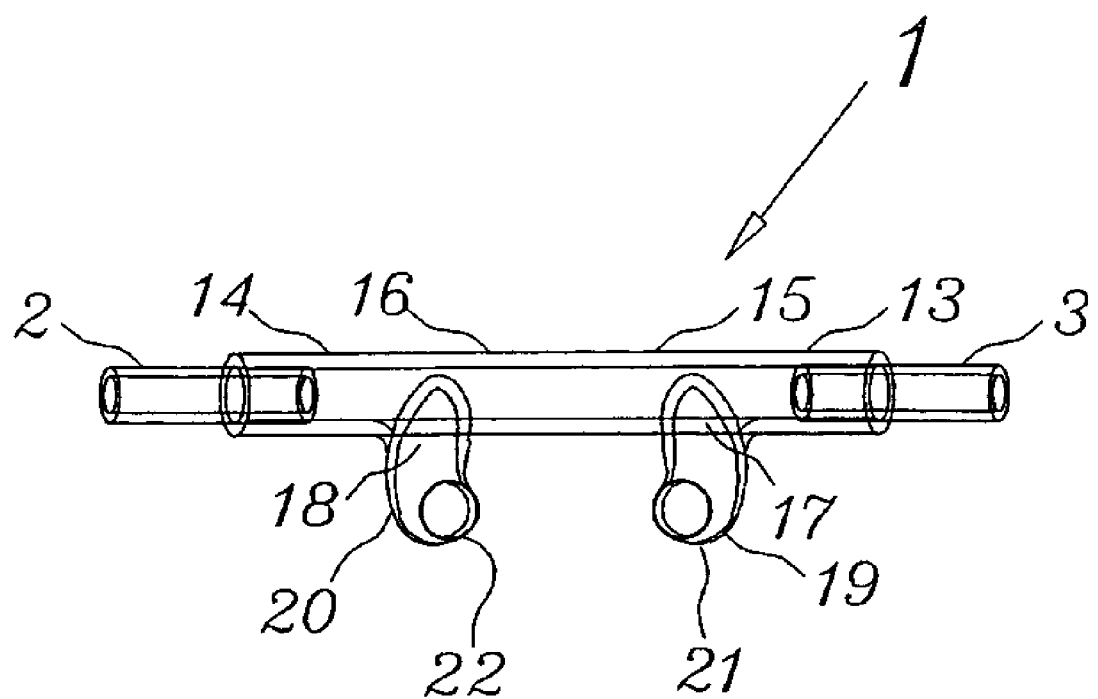
FIG. 3 is a top view of the present invention. The material is transparent and inner surfaces can be seen.

The novel nasal cannula assembly will now be described by referring to the drawings. In FIG. 1, the cannula assembly, generally designated numeral 10 is illustrated in position on a patient's face. The assembly comprises nasal cannula 1, a pair of support tubes 2 and 3 connected to opposite ends of the cannula, main oxygen supply line 6, fork connector 5 for joining support tubes 2 and 3 to main supply tube 6 and a slip loop 4 disposed about support tubes 2 and 3. The structure of cannula 1 is best understood by viewing FIGS. 3-5. The composition of the cannula is preferably of a thermoplastic composition such as polyvinyl chloride or polyvinyl acetate that are quite pliable or flexible and is normally fabricated using a dip molding process, although the shape of the cannula is suitable for injection molding. The plasticizer used to add flexibility is preferably one that resists migration from the cannula to the skin.

The cannula is generally a hollow tubular member having an opening at each end and is of a length approximately twice the width between an average patient's nostrils. Cannula 1 has a main body portion 15 and 16 formed at an acute angle B, preferably 120 to 160 degrees, and having a pair of spaced, hollow tubular extensions 19 and 20 integral with and projecting outwardly from the main body portion. The tubular extensions 19 and 20 terminate in gas direction orifices 17, 18 with the hollow portion of the extensions communicating with the hollow main body portion.

The main body 15 and 16 lies in a first plane with end portions 13 and 14 lying essentially in the same plane. The axis of end portion 13 is essentially collinear with the axis of main body portion 15 and the axis of end portion 14 is essentially collinear with the axis of main body portion 16. The open ends of end portions 13 and 14 have an inside diameter that receives the open ends of support tubes 2 and 3 that are friction fitted or bonded in place therein.

Figure 4:
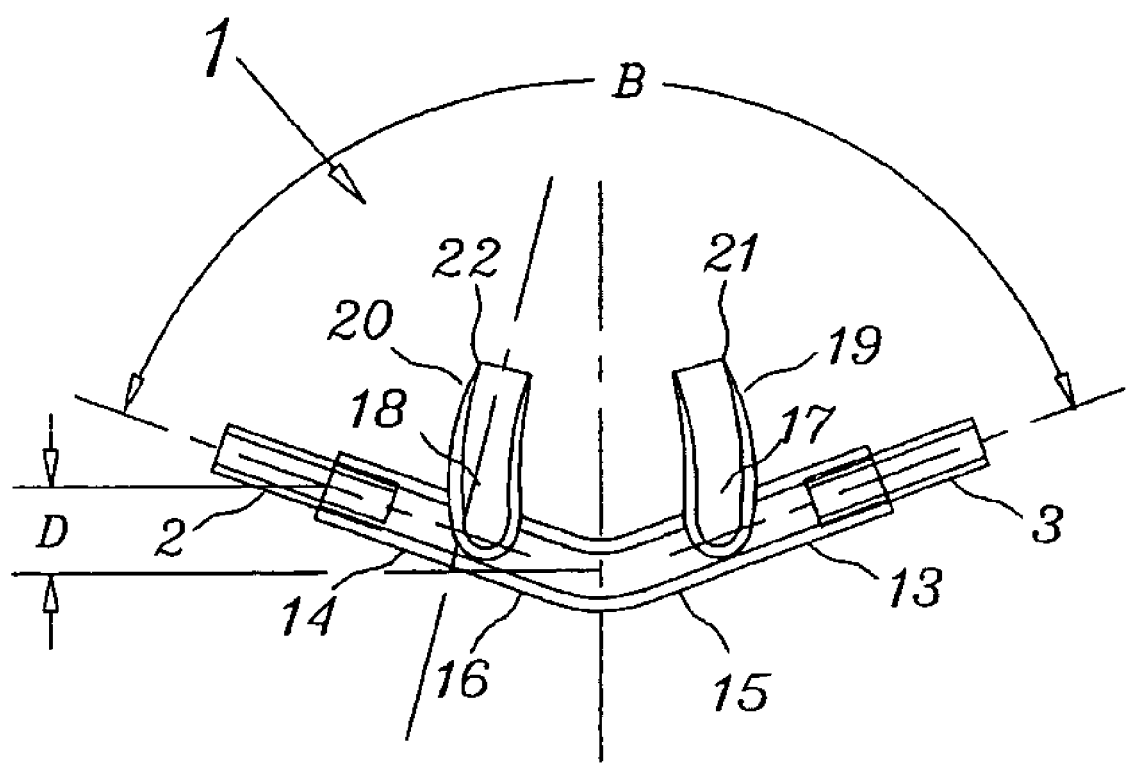
FIG. 4 is a front view of the present invention that shows the inward curvature of the nares.
Figure 5:
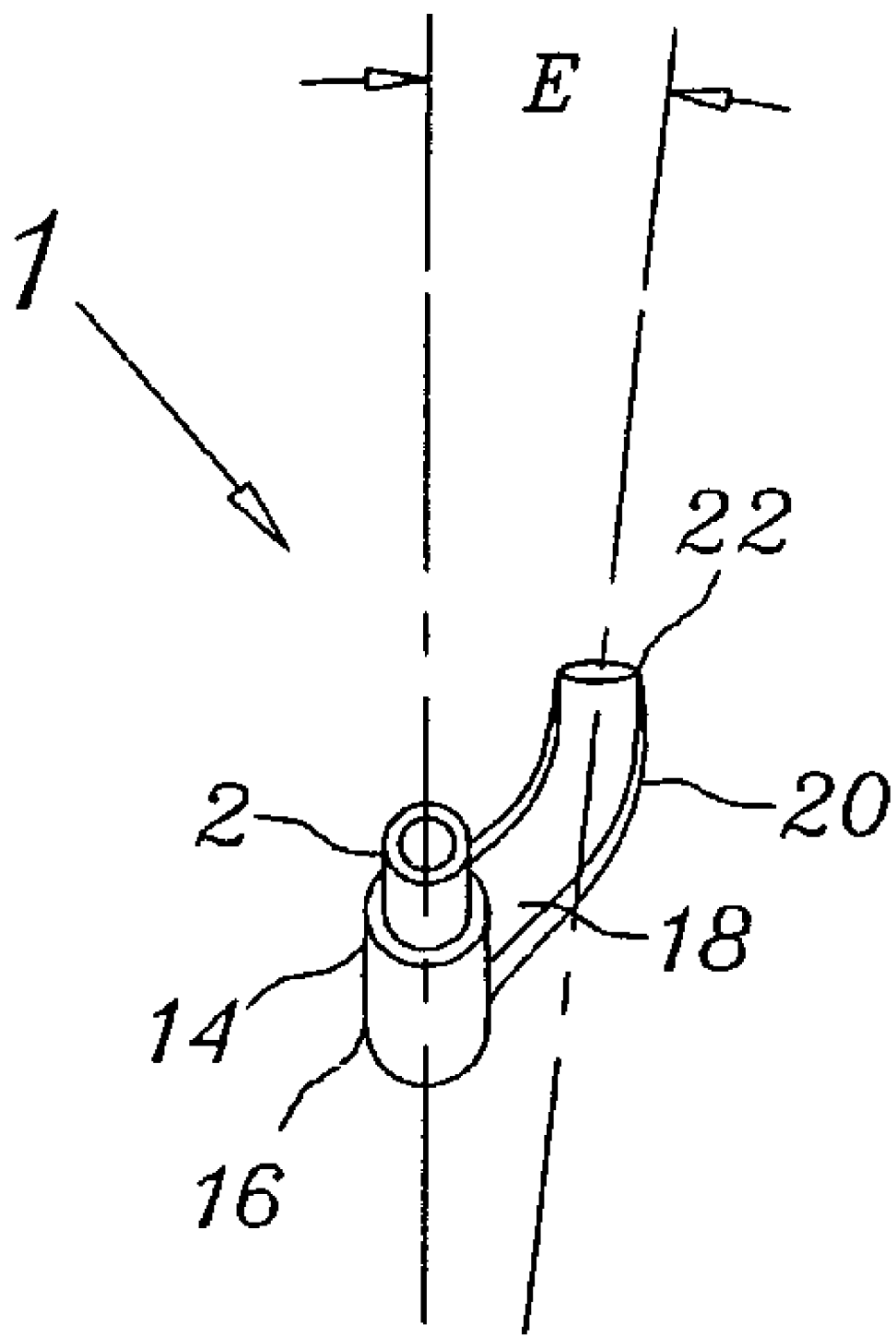
FIG. 5 is a side view of the present invention. Some of the inner surfaces were removed to clarify the drawing.

The shape of tubular extensions 19 and 20 is describable only in a three-dimensional sense and must therefore be shown by two figures, these being FIGS. 4 and 5. It can be seen from FIG. 5 that the tubular extensions join the main body at an angle of approximately 45 degrees from the first plane then curve upward with the longitudinal axis of the open end of extension 20 and lying in a second plane nearly parallel to the first plane at a small angle E, ranging from 0 to 10 degrees and displaced from first plane approximately 0.25 inches.

Figure 6:
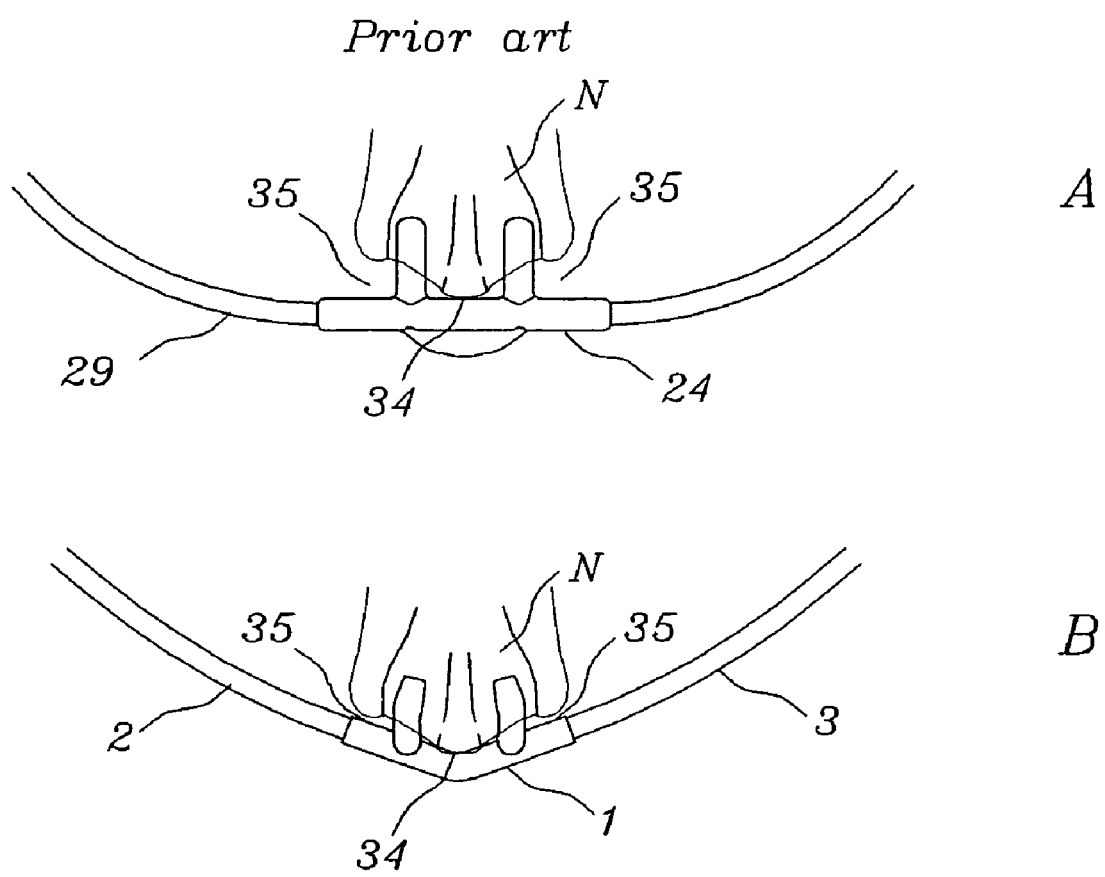
FIG. 6 shows a comparison of a prior art cannula and the cannula of the present invention as they sit in place under the nose.

FIG. 4 shows an inward curvature of the extensions not visible in FIG. 5 where the longitudinal axis of 19 and 20 form an acute angle C, ranging from 6 to 20 degrees to a central plane. This curve matches the natural contour of the nasal passages and increases the distance between the open ends of the extensions and the nasal walls and directs gas flow into the open space of nasal cavity N instead of against the nasal walls. FIG. 6B shows the present invention as compared to prior art cannulas illustrated in FIG. 6A.

FIGS. 4 and 5 show the wall thickness of the tubular extensions 19 and 20 decreasing towards open ends 22 and 21. The thickness at the end is less than 0.006 inches and the walls will yield to nasal hairs thereby reducing sensation.

Figure 7:
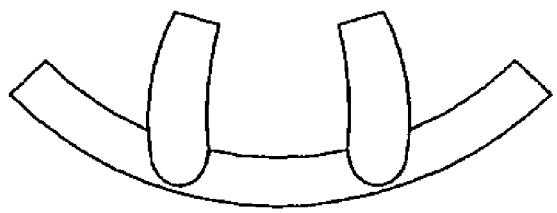
FIGS. 7A, B, C and D are various embodiments of the present invention.
Figure 7:
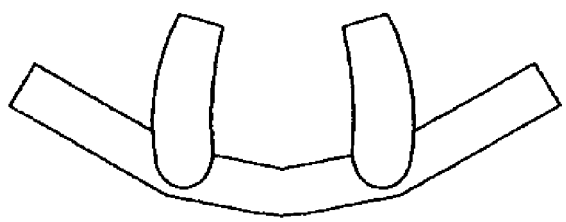
Figure 7:
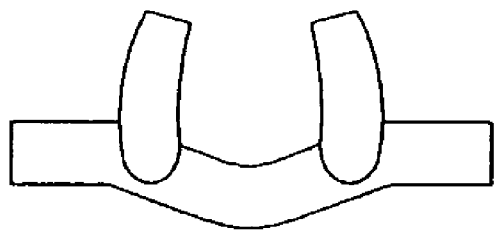
Figure 7:
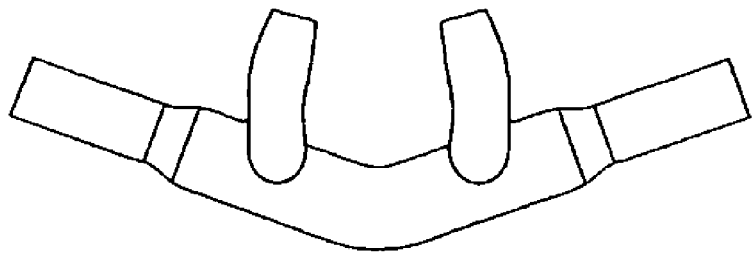
Figure 8:
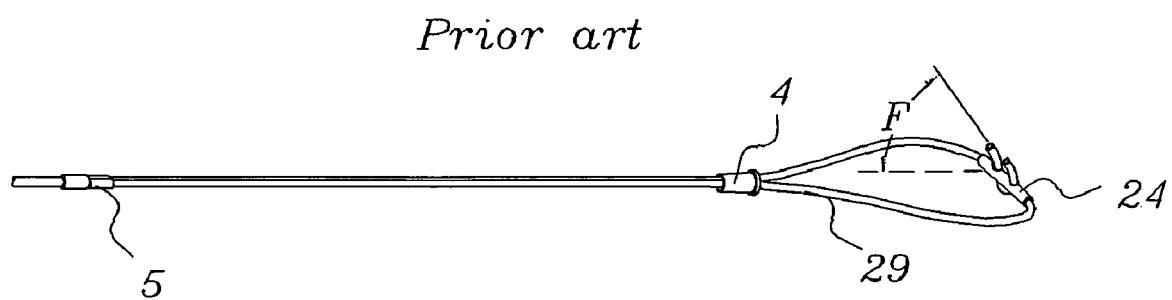
FIG. 8 shows a prior art injection molded cannula in the proper position for bonding during manufacture.
Figure 9:
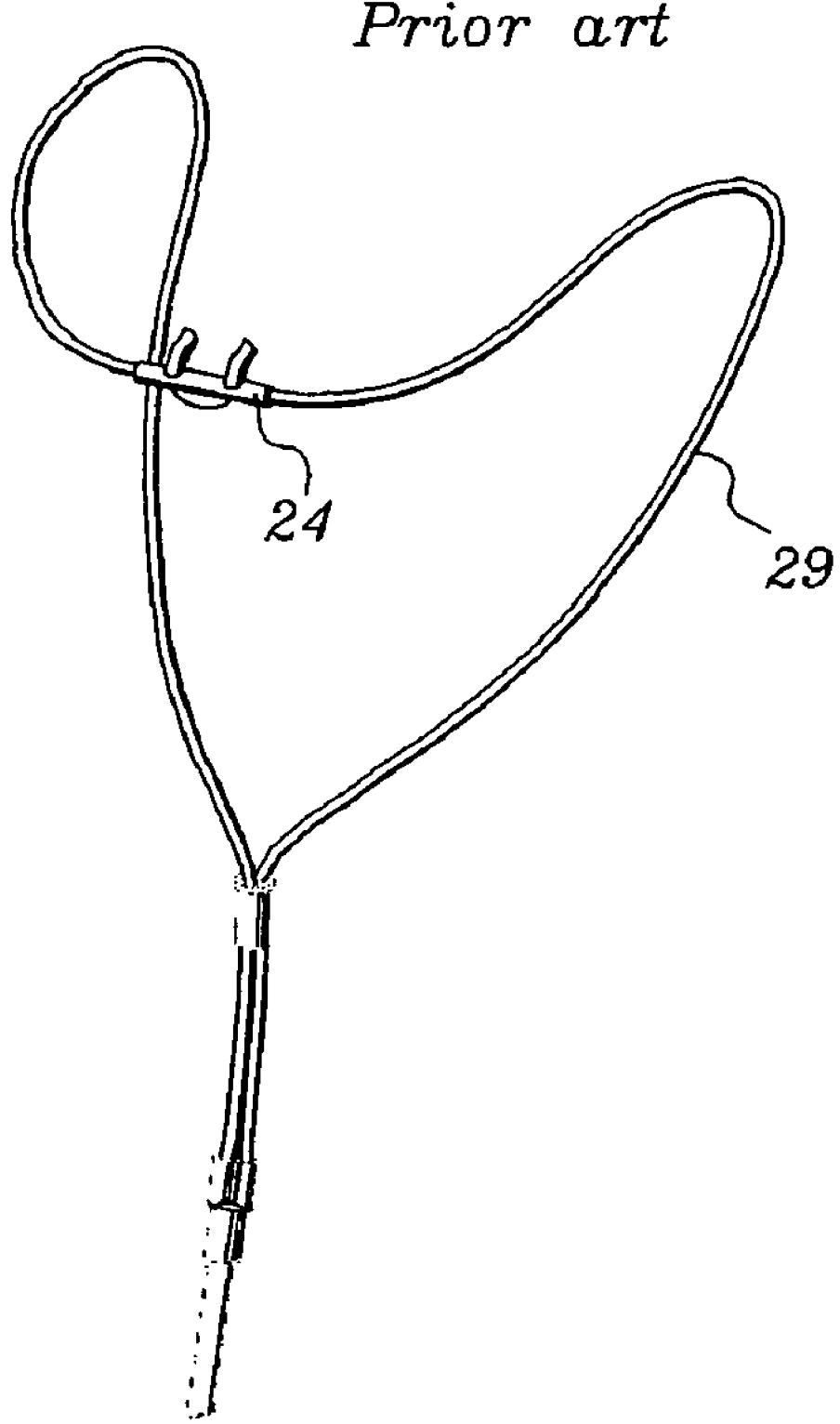
FIG. 9 shows a prior art cannula and the shape the tubing adopts after a period of time due to a material property known as memory.
Figure 10:
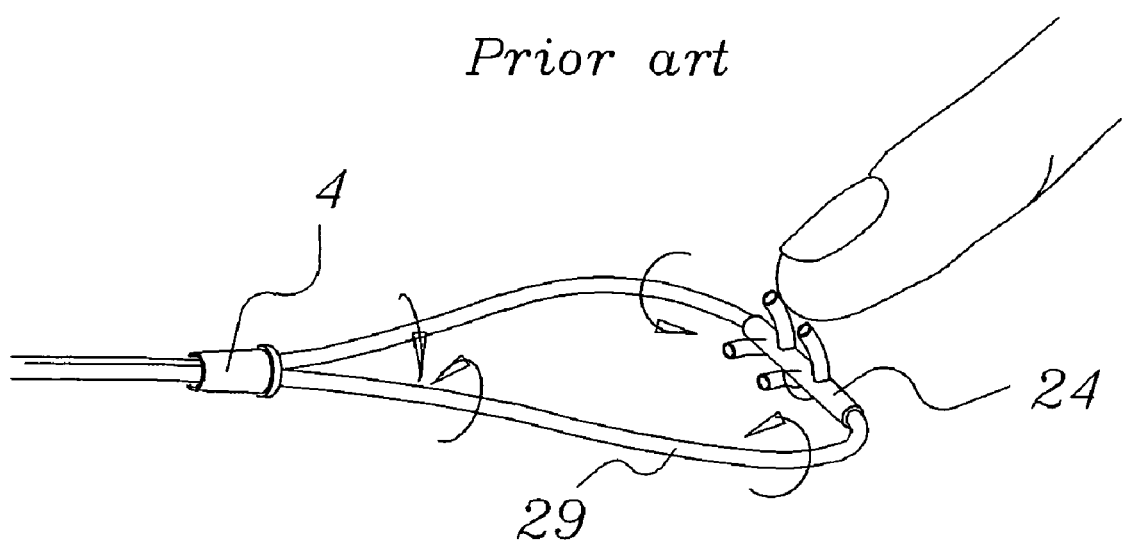
FIG. 10 illustrates the characteristic of prior art cannulas to resist rotation through torsional stiffness offered by the tubing.

FIGS. 7A, B, C and D are various embodiments of the present invention. FIG. 7A has a main body portion and end portions formed in a continuous arc that performs essentially the same function as a vee shape. FIGS. 7B and C are examples of cannulas with end portions having longitudinal axes at a different angle from the axes of the main body portion but still have an acute angle that stabilizes the cannula on the face. FIG. 7D is a cannula with reduced diameters at the outer ends of the arms. This is useful if it is desirable to increase the body diameter to facilitate the fabrication of dip molding forms. It can also be used for reduced diameter tubing meant to reduce visibility for cosmetic reasons.

FIG. 6A shows a prior art cannula 24 resting under the nose at point 34 leaving clearance 35 for the cannula to tip to the side allowing the nares to contact the nasal walls or even come out. FIG. 6B shows cannula 1 of the present invention in place under a nose with minimal clearance 35 preventing significant rocking of the cannula about point 34.

Figure 2:
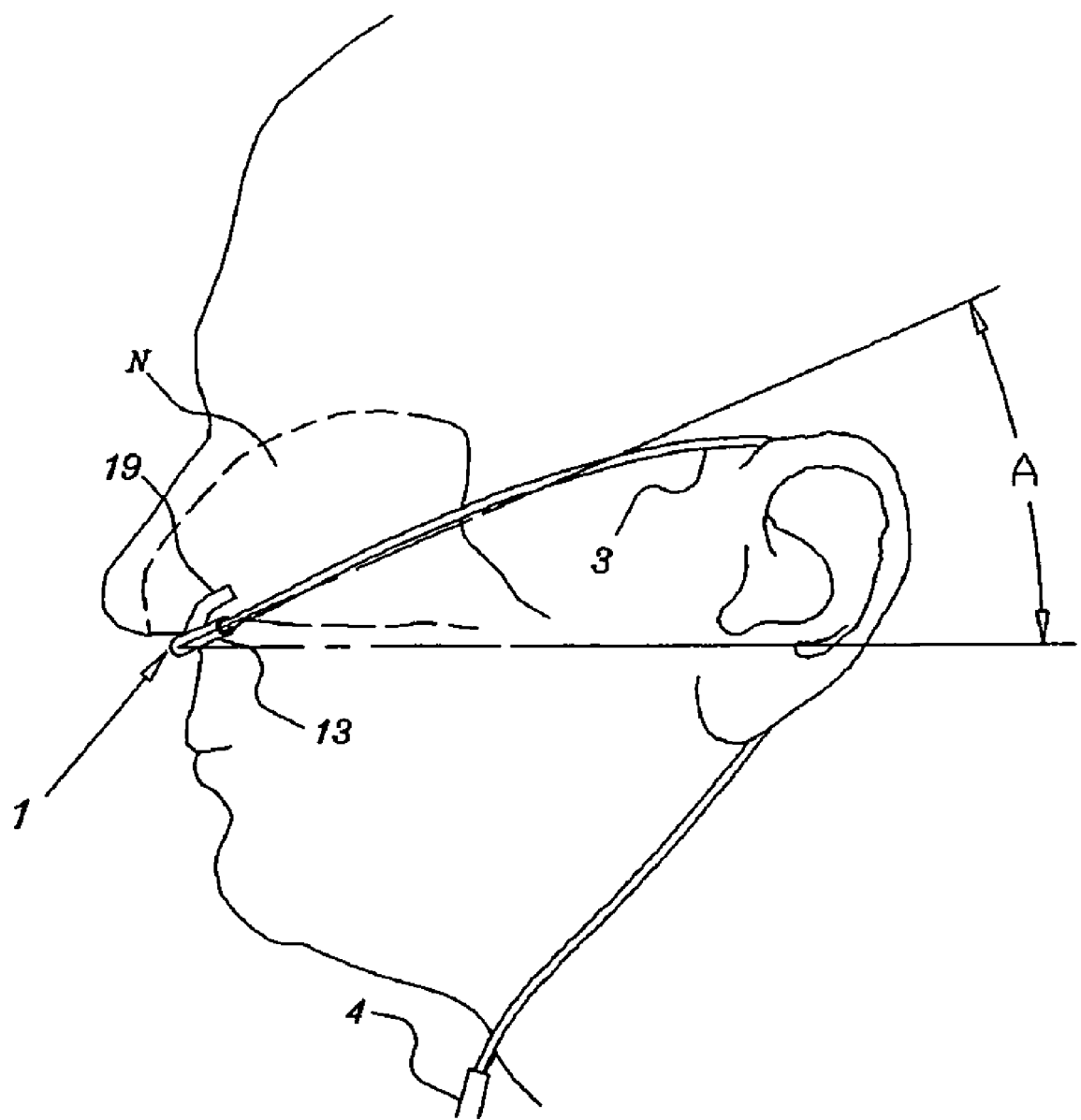
FIG. 2 is a side view of the present invention in position on the face and showing the orientation of the nares 19 in the nasal cavity N. It illustrates how the support tubing 3 rotates the cannula 1 until the arms 13 are directed towards the top of the ear in line with the tubing.

FIGS. 1 and 2 illustrate the preferred manner in which the cannula assembly is worn by a patient. The cannula 1 rests across the patient's nasalabidial area and the flexible support tubes 2 and 3 are directed across the patient's face, over and behind the ears, down the jaw areas and brought together under the chin. A slip loop 4 of sufficient size to encompass both support tubes may then be adjusted so that the cannula 1 will remain firmly in place without the tubes being unduly taut.

Vertical distance D, shown in FIG. 4, from the center of main body to the outer ends of arms 13 and 14 is a lever arm that will transform tension from the support tubing into torque that can rotate the cannula about an axis. This axis of rotation is generally through the point where the cannula contacts the philtrum directly under the nose.

FIG. 2 shows the cannula body and nasal extension 19 rotated to angle A as a result of arm 13 and support tubing 3 pointing substantially tangential to the top of the patient's ears. The oxygen supply is therefore guided throughout administration directly into nasal cavity N.

When the cannula of the present design is combined with flexible support tubing, the cannula body can be made with much thinner walls that flex more easily and is lighter in weight. Cannulas used with prior art tubing must be sufficiently thick to resist bending or kinking from the forces exerted by the coiled tubing in the package and this increases the weight.

Perhaps the most important feature of the cannula of the present invention is that it can be used with extremely flexible support tubing that bends freely with head movements without disturbing the position of the cannula on the face. The combination of flexible tubing and the form fitting shape and light weight of the cannula keeps it in place with almost no tubing tension that, all at once, reduces sores on the ears, nose and neck and eliminates grooves across the cheeks. It must be noted that the cannula of the present invention is well suited for use with prior art support tubing and offers significant improvements in comfort over all types of prior art cannulas. However some features, most notably low wall thickness, are not suitable for use with prior art support tubing.

The special support tubing used with the cannula of the present invention was chosen after extensive experimentation with a number of different materials and variations of materials. The considerations included flexibility, manufacturability, service life, packaging, smell, skin compatibility, medical compatibility, toxicity, cost and availability.

The support tubing is typically 2 pieces, approximately ⅛" outside diameter and 21 inches in length and has at least one of the following properties (i) compression set less than 45% at 23 degrees C. per ASTM D-395 (ii) 10% tensile modulus of 200 psi or less (iii) brittle temperature less than minus 40 degrees C. per ASTM D-746 (iv) hardness from 40 to 75 durometer on the Shore A scale.

The 10% tensile test is not normally found in published data but is necessary to quantify an important property of the tubing. The values for tensile stress were acquired by suspending weights from a 13" length of tubing and adding weight until the length increased to 14.3". The weight is divided by the unstretched cross sectional area of the tubing to get the tensile stress in pounds per square inch or psi.

Typical values for prior art tubing extruded from Teknor-Apex 3300-82 PVC compound are a 10% tensile modulus of 450 psi, brittle point temperature −30 C., compression set greater than 50% and hardness 82 Shore A.

The preferred tubing material is a PVC compound that uses at least some high and/or ultra high molecular weight PVC resin. High molecular weight resin has an average molecular weight of at least 100,000 and ultra high molecular weight resins have weights of 150,000 or higher while regular PVC resins used in prior art tubing have a range of average molecular weight between 30,000 and 75,000. The higher molecular weight resins give compounds lower compression set, improved low temperature properties and elasticity or stretchiness, all of which are desirable for the present invention. It can be solvent bonded the same as regular PVC so existing manufacturing processes can be used. Preferably the compound would contain low extractable plasticizers that resist migration from the tubing to the oils on the skin.

The invention of support tubing with the aforementioned properties can be used with any cannula that does not rely on the tubing to maintain the proper rotational angle of the nares. An unsuitable cannula is one that has the support tubing bonded along the rotational axis and/or does not bend in a preferential plane.

At least 3 types of cannula bodies are compatible with the flexible tubing of the present invention. All can be oriented properly as a result of tension or direction of the support tubing. The first is cannula that bends about the face in a defined plane such that the nares are properly oriented. Another type is a cannula that has arms bonded at points offset from the axis of rotation, effectively forming a crank that rotates the cannula when pulled by the tubing. Yet another type is a cannula body with a low center of gravity that naturally orients itself with the nares towards the top when hung from the support tubing.

In addition to the invention of the cannula and the invention of the support tubing is an invention for main supply tubing that is very manageable, drapes nicely and resists the formation of twisted loops that blocks flow in prior art tubing. The main supply tubing 6 of FIG. 1 is approximately ¼ inches diameter and between one and 35 feet long. The material is generally the same flexible material used for the support tubing.

Figure 11:
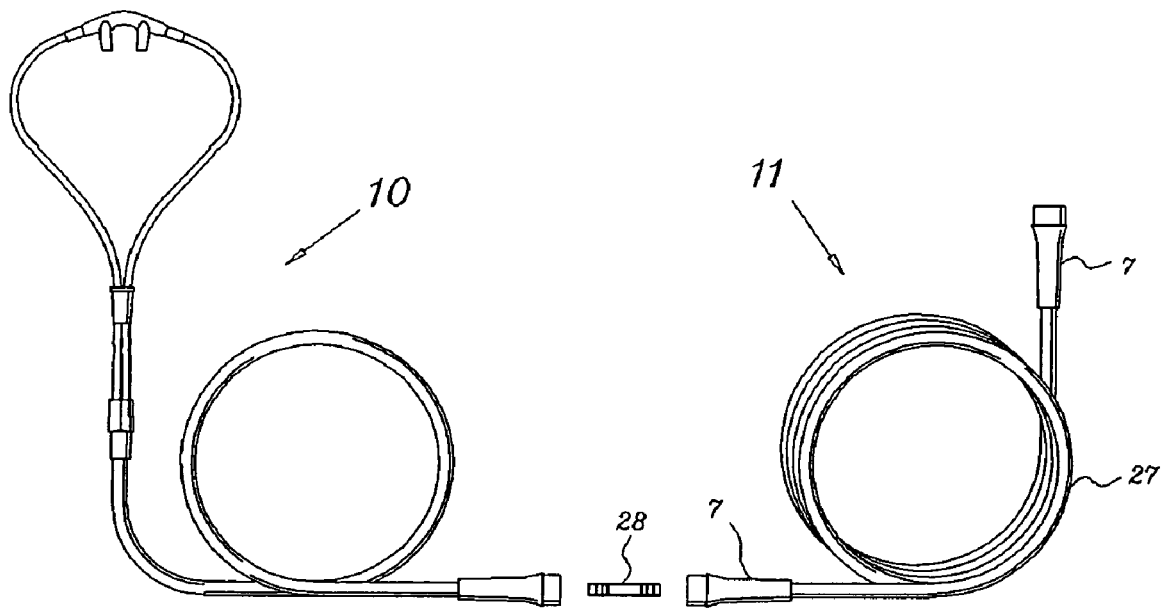
FIG. 11 shows a cannula assembly and a detachable extension hose with a coupler to join the two sections.

Generally, when the length of the main supply tubing is 25 feet or more a major portion is detachable so it can be reused when a new cannula is needed. FIG. 11 illustrates typical nasal cannula assembly 10 and detachable extension tubing assembly generally denoted as 11. The extension tubing assembly consists of a length of hollow conduit 27 with connectors 7 affixed to both open ends.

Hollow conduit 27 is generally the same material as main supply tubing 6 used in the cannula assembly although it may be a harder durometer to better withstand blockage from footsteps. One end of rigid hollow tubular adaptor 28 is inserted into the end connector of cannula assembly 10 and the other end is inserted into one of the connectors 7 of extension assembly 11 so that the free end of 11 is in communication with the nares of cannula assembly 10. In most cases, the free end is connected to a gas source, most often oxygen.

The invention claimed is:

1. A nasal cannula assembly designed for contact with the nasalabidial area of a patient's nose and comprising:
    a hollow tubular member having an opening at each end, said tubular member having a central portion of sufficient length to span the width of an average patient's nostrils and end portions extending from each end of said central portion, said central portion having a pair of spaced, hollow extensions integral with and projecting therefrom said hollow extensions terminating in gas directing orifices and which hollow portion of said extensions communicate with said hollow tubular member,
    said central portion lying in a first plane with longitudinal axes symmetrical about a midpoint and forming an angle in said first plane less than 160 degrees,
    each said hollow extension having a longitudinal axis projecting from said central portion at an acute angle from said first plane, said gas directing orifices of said hollow extensions having a longitudinal axis lying in a second plane essentially parallel to and displaced from said first plane,
    said end portions of said central portion lying in essentially the first plane with longitudinal axis of said end portion essentially collinear with longitudinal axis of corresponding symmetrical half of said central portion.

2. A nasal cannula assembly as recited in claim 1, wherein said hollow extensions terminate in said gas directing orifices where thickness of material forming rim of said orifices is less than 0.006 inches.

3. A nasal cannula assembly as recited in claim 1, wherein the longitudinal axis of each said gas directing orifice is angled in said second plane toward second said gas directing orifice such that the longitudinal axes of each said gas directing orifice intersect at an acute angle.

4. The nasal cannula assembly of claim 1 further comprising at least one support tube having a 10% tensile modulus less than 200 psi.

5. A nasal cannula assembly as recited in claim 4 wherein said support tubes have a hardness between 40 and 75 Shore A.

6. A nasal cannula as recited in claim 4 wherein said support tubes have a compression set less than 45% at 23 degrees C. per ASTM D-395.

7. A nasal cannula assembly as recited in claim 4 wherein said support tubes have a brittle temperature less than −40 degrees C. per ASTM D-746.

8. A nasal cannula assembly as recited in claim 4 wherein said support tubes are manufactured from a polyvinyl chloride compound comprising at least a portion of polyvinyl chloride resin having an average molecular weight of at least about 100,000.

9. A nasal cannula designed for contact with the nasalabidial area of a patient's nose and comprising:
    a hollow tubular member having an opening at each end, said tubular member having a central portion of sufficient length to span the width of an average patient's nostrils and end portions extending from each end of said central portion,
    said central portion having a pair of spaced hollow extensions integral with and projecting therefrom, said hollow extensions terminating in gas-directing orifices and which hollow portion of said extensions communicate with said hollow tubular member,
    said central portion lying in a first plane with longitudinal axes symmetrical about a midpoint, wherein said midpoint is opposite the said hollow extensions and noncollinear with the center points of the open ends of said hollow tubular member,
    each said hollow extension having a longitudinal axis projecting from said central portion at an acute angle from said first plane, said gas-directing orifices of said hollow extensions having longitudinal axes lying in a second plane parallel to and displaced from said first plane,
    shape of said hollow tubular member and length of said end portions selected to cause the center-of-gravity of said cannula to lie below said center points of the open ends of said hollow tubular member.

10. A nasal cannula as recited in claim 9, wherein shape of said central portion of said hollow tubular member forms a "V" and said end portions of said hollow tubular member lie in said first plane with longitudinal axis of said end portion collinear with longitudinal axis of corresponding symmetrical half of said central portion.

11. A nasal cannula as recited in claim 9, wherein shape of said central portion of said hollow tubular member forms a "V" and said end portions of said hollow tubular member lie in said first plane with longitudinal axis of first said end portion collinear with longitudinal axis of second said end portion.

12. A nasal cannula as recited in claim 9, wherein said shape of said hollow tubular member is a circular arc lying within said first plane.

13. A nasal cannula as recited in claim 9, wherein said hollow extensions terminate in said gas-directing orifices where thickness of material forming rim of said orifice is less than 0.006 inches.

14. A nasal cannula as recited in claim 9, wherein the longitudinal axis of each said gas-directing orifice is angled in said second plane toward second said gas-directing orifice such that the longitudinal axes of said gas-directing orifices intersect at an acute angle.

15. A nasal cannula assembly designed for contact with the nasalabidial area of a patient's nose comprising:
    a nasal cannula as recited in claim 10, 11, or 12,
    at least one support tube having a 10% tensile strength modulus less than 200 psi,
    a main supply tube.

16. A nasal cannula assembly as recited in claim 15 wherein said support tubes have a hardness between 40 and 75 Shore A.

17. A nasal cannula assembly as recited in claim 15 wherein said support tubes have a compression set less than 45% at 23 degrees C. per ASTM D-395.

18. A nasal cannula assembly as recited in claim 15 wherein said support tubes have a brittle temperature less than −40 degrees C. per ASTM D-746.

19. A nasal cannula assembly as recited in claim 15 wherein said support tubes are manufactured from a polyvinyl chloride compound comprising at least a portion of polyvinyl chloride resin having an average molecular weight of at least 100,000.

20. A nasal cannula assembly designed for contact with the nasalabidial area of a patient's nose comprising:
   a nasal cannula as recited in claim 10, 11, or 12,
   at least one support tube,
   a main supply tube having 10% tensile modulus less than 200 psi.

21. A nasal cannula assembly as recited in claim 20 wherein said supply tube has a hardness between 40 and 75 Shore A.

22. A nasal cannula assembly as recited in claim 20 wherein said supply tube has a compression set less than 45% at 23 degrees C. per ASTM D-395.

23. A nasal cannula assembly as recited in claim 20 wherein said supply tube has a brittle temperature less than −40 degrees C. per ASTM D-746.

24. A nasal cannula assembly as recited in claim 20 wherein said supply tube is manufactured from a polyvinyl chloride compound comprising at least a portion of polyvinyl chloride resin having an average molecular weight of at least 100,000.

* * * * *